US00PP11314P

United States Patent [19]

Verwer

[11] Patent Number: Plant 11,314

[45] Date of Patent: Mar. 28, 2000

[54] DAHLIA PLANT NAMED 'GALLERY ART NOUVEAU'

[75] Inventor: Aad Verwer, Lisse, Netherlands

[73] Assignee: Fa. Gebr. Verwer, Lisse, Netherlands

[21] Appl. No.: 09/026,011

[22] Filed: Feb. 19, 1998

[30] Foreign Application Priority Data

Apr. 7, 1997 [NL] Netherlands ..... DHL 81

[51] Int. Cl.[7] ..... A01H 5/00

[52] U.S. Cl. ..... Plt./321

[58] Field of Search ..... Plt./321

[56] References Cited

U.S. PATENT DOCUMENTS

P.P. 10,496 7/1998 Verwer ..... Plt./321

P.P. 10,497 7/1998 Verwer ..... Plt./321

P.P. 10,510 7/1998 Verwer ..... Plt./321

OTHER PUBLICATIONS

GTITM UPOVROM Citation for 'Gallery Art Nouveau' as per NL PBR DHL0081; Apr. 7, 1997.

*Primary Examiner*—Howard J. Locker

*Assistant Examiner*—Kent L. Bell

*Attorney, Agent, or Firm*—Christie, Parker & Hale, LLP

[57] ABSTRACT

A compact growing, continuously flowering perennial dahlia plant producing pink/purple flowers.

1 Drawing Sheet

BACKGROUND OF THE INVENTION

The present invention relates to a new and distinct variety of *Dahlia hybrida* known by the varietal denomination 'Gallery Art Nouveau'.

'Gallery Art Nouveau' is a naturally occurring branch sport of the variety 'Gallery Art Deco', U.S. Plant Pat. No. 10,525.

SUMMARY OF THE INVENTION

The new variety is a dahlia plant with low growing habit which produces attractive pink/purple flowers against a background of abundant medium green foliage. The continuous flowering perennial plant is compact and suitable for use as a pot plant and for outdoor gardens. Inflorescences are compact and extend above the foliage borne on relatively short peduncles. Plant height is about 30 cm. Roots of cuttings of the new variety are initiated in about 4 days at 20° C. and a rooted cutting is produced in about 14 days at 20° C. The rooting habit is such that fine roots are produced first and then become fleshy. Among the traits possessed by the new variety which in combination distinguish it from other varieties known to the inventor are its compact plant habit and flower color and continuous flowering during the growing season.

Asexual reproduction by cuttings of the new variety in The Netherlands has demonstrated that the combination of characteristics as described herein for 'Gallery Art Nouveau' are firmly fixed and are retained through successive generations of asexual reproduction.

COMPARISON WITH PARENT

The new variety differs from its parent in flower color. Whereas flowers of 'Gallery Art Deco' are burnt orange, flowers of 'Gallery Art Nouveau' are pink/purple.

BRIEF DESCRIPTION OF ILLUSTRATION

The accompanying color photographic illustration shows a typical plant of the new variety in colors as nearly true as possible with an illustration of this type. The illustration depicts growth habit, flower position relative to leaves and flower color.

DESCRIPTION OF THE NEW VARIETY

In the following description, color references are to The Royal Horticultural Society Colour Chart, where color values refer to color plate numbers in this chart.

The following observations are of plants described and grown in The Netherlands under greenhouse and outdoor conditions which approximate those generally used in commercial practice.

'Gallery Art Nouveau' has not been observed under all possible environmental conditions. The phenotype may vary with variations in environment such as temperature, light intensity, day length and cultural conditions.

Parentage: Naturally occurring branch sport of 'Gallery Art Deco'.

Growing conditions: Useful growing conditions include day temperature of about 15° to 22° C. and night temperature about 10° to 15°C. with normal daylight about 14 hours. Plants grow normally June to September in The Nethlerlands. No growth regulator treatments are required.

Plant:

*Plant shape.*—Rounded.

*Growth habit.*—Spreading.

*Height.*—About 30 cm.

*Growth rate.*—Rapid.

*Branching characteristics.*—Freely branching.

*Vigor.*—Vigorous.

*Crop time.*—About 60 days.

*Hardiness.*—Plants are winter hardy to 0° C.

*Disease resistance.*—Similar to the species.

Foliage:

*Arrangement.*—Opposite.

*Type.*—Compound and single.

*Leaves.*—Quantity of leaves: Many. Leaflets: Leaf arrangement opposite, simple or compound; compound leaves have either three or five leaflets; leaf size — single, about 5.4 cm long, about 3.7 cm wide; compound about 12 cm long, about 9 cm wide. Shape: Ovate. Tip: Acute, acuminate. Base: Cordate. Attachment: Stalked, petioled.

*Petiole length.*—About 1 to 3 cm.

*Margin.*—Pentate.

*Texture.*—Smooth.

*Pubescence upper side.*—None.

*Pubescence under side.*—Little.

*Color.*—Young foliage: Upperside near 137C; under side near 191A. Mature foliage: Upperside near 139A; under side near 191A. Petiole: Near 138A, with anthocyanin coloration. Venation: Upperside near 146A; under side near 146D.

*Venation.*—Pinnate.

Flower:

*Habit.*—Recurrent, continuous during season.

*Form.*—Decorative.

*Natural flowering season.*—July until November (first frost).

*Quantity of flowers per stem.*—Usually 1.

*Diameter.*—About 110 mm.

*Depth.*—About 30 mm.

*Longevity on plant.*—About 10 days.

*Longevity as cut flower.*—About 7 days.

*Persistent or self-cleaning.*—Persistent.

*Fragrance.*—None.

*Ray florets.*—Appearance: Shiny. Shape: Elliptic. Margin: Entire. Tip: Obtuse. Length: About 55 mm. Width: About 15 mm. Color: When opening: Near 187A. Upperside: Near 66C. Under side: Near 61A. Fading to: Near 62B (faded ray floret). After senescence: Near 179C.

*Peduncle or flower stem.*—Length: About 10 to 15 cm. Color: Near 144B, anthocyanin coloration near 183B. Strength: Strong. Angle: Erect. Pubescence: None.

*Bud.*—Length: About 10 mm. Diameter: About 15 mm. Shape: Globular. Rate of opening: Opens in about 14 days. Color: Near 145A.

*Sepals.*—Appearance: Satiny. Texture: Smooth. Arrangement: In circle. Number: About 25. Length: About 1.5 cm. Width: About 0.7 cm. Shape: Ovate. Margin: Entire. Apex: Acute. Base: Rounded. Color: Upperside near 137A; under side near 137C.

*Disc florets.*—Number: About 45. Length: About 1.1 cm. Color: Near 7A. Shape: Cylindric.

*Calyx.*—Small.

*Stamens.*—Number: Many. Anther shape: Long, pointed. Anther size: Less than 1 mm. Anther color: Near 14A. Pollen color: Near 17B.

*Pistils.*—Number: Many. Stigma shape: Divided, forked. Stigma color: Near 14A. Style color: Near 154B. Style length: About 4 mm. Ovary number: 1 per pistil.

*Other characteristics.*—Ray florets are bent downwards.

I claim:

1. A new and distinct dahlia plant of the variety substantially as shown and described.

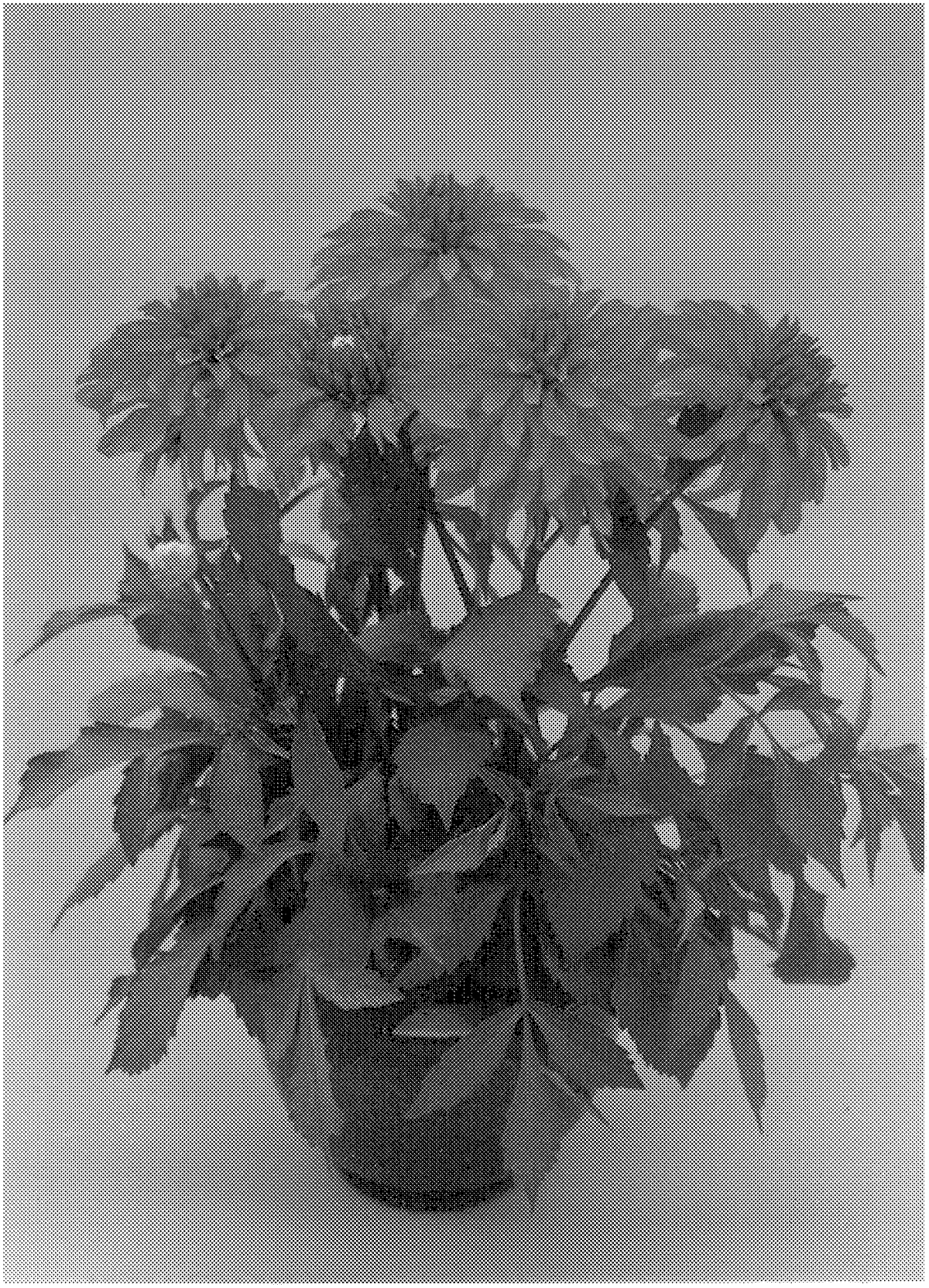

* * * * *